United States Patent [19]

Dollat et al.

[11] Patent Number: 5,500,415
[45] Date of Patent: Mar. 19, 1996

[54] PROCESS FOR THE PREPARATION OF SPHERULES OF ACTIVE PRINCIPLES AND EMULSIONS CONTAINING THE SPHERULES

[75] Inventors: Jean-Marie Dollat, Montlucon; Marc Molin, Neris Les Bains; Pascal Theallier, Montlucon, all of France

[73] Assignee: Rhone-Poulenc Nutrition Animale, Antony, France

[21] Appl. No.: 220,358

[22] Filed: Mar. 31, 1994

[30] Foreign Application Priority Data

Mar. 31, 1993 [FR] France ................... 93 03728

[51] Int. Cl.⁶ .............. A61K 9/16; A61K 9/64; C07K 1/32; C07K 14/435
[52] U.S. Cl. .............. 514/21; 530/354; 530/410; 530/419; 530/427; 424/456; 424/492; 548/303.7; 544/327; 552/653; 562/569; 568/824
[58] Field of Search ............... 514/21, 387; 530/354, 530/410, 412, 419, 417, 427; 424/455, 456, 452; 568/824; 562/569; 545/408; 552/653, 299; 546/301; 544/327, 328, 329, 251; 548/303.7

[56] References Cited

U.S. PATENT DOCUMENTS

| | | | |
|---|---|---|---|
| 2,828,202 | 3/1958 | Rosenberg | 75/236 |
| 3,202,731 | 8/1965 | Grevenstulr et al. | 264/7 |
| 3,956,172 | 5/1976 | Saeki et al. | 264/4.3 |
| 4,929,774 | 5/1990 | Fukamachi et al. | 568/824 |
| 5,035,896 | 7/1991 | Apfel et al. | 424/456 |

FOREIGN PATENT DOCUMENTS

| | | |
|---|---|---|
| 0261616A2 | 3/1988 | European Pat. Off. |
| 0285682A1 | 10/1988 | European Pat. Off. |
| 2468401 | 5/1981 | France |
| 1188957 | 4/1970 | United Kingdom |
| 1200906 | 8/1970 | United Kingdom |

*Primary Examiner*—Michael G. Wityshyn
*Assistant Examiner*—Nancy J. Degen
*Attorney, Agent, or Firm*—Finnegan, Henderson, Farabow, Garrett & Dunner

[57] ABSTRACT

A process for the preparation of spherules and emulsions containing such spherules. A primary oil-in-water emulsion is formed containing particles comprising one or more active principles in oily form suspended in water, the water optionally containing at least one protein. Controlled division of the primary emulsion is achieved by combining the primary emulsion with a water-immiscible solvent to create a second emulsion containing spherules of the primary emulsion. Preferably, the particles of the primary emulsion have mean diameters of about 1 μm, and preferably, the spherules contained in the second emulsion have a diameter ranging from 100 μm to 500 μm. If protein is contained in the primary emulsion, the protein can be cross-linked. Further, the spherules can be separated from the water-immiscible solvent.

22 Claims, 4 Drawing Sheets

PROCESS FOR THE PREPARATION OF SPHERULES OF ACTIVE PRINCIPLES AND EMULSIONS CONTAINING THE SPHERULES

The present invention relates to a new process for the stabilization of alimentary and/or medicamentous, i.e. medicinal, active principles. It also relates to a process for the preparation of spherules of active principles which can be very finely dispersed.

Representative alimentary and/or medicinal active principles which may be used for preparing the spherules according to the invention, include (1) vitamins, such as vitamin A, vitamin E, vitamin $B_{12}$, vitamin H or biotin, vitamin $D_3$, vitamin PP, vitamin $K_3$ or menadione, vitamin $B_1$ or thiamine, vitamin $B_2$ or riboflavin, vitamin $B_3$ or niacin, vitamin $B_5$ or pantothenic acid and vitamin $B_6$ or pyridoxine, (2) carotenoids, such as β-carotene, astaxanthine and canthaxanthine, and (3) enzymes, such as β-glucanase and xylanase.

Of the vitamins, it is preferred to stabilize vitamins A and E.

Vitamins A and E are widely used in animal nutrition for promoting animal growth. Since animal feeds are often prepared by a process which consists in forming particles by the joint action of pressure and heat, heat and pressure-sensitive active principles such as Vitamin A cannot undergo this procedure without suffering serious degradation.

To preserve vitamin A, for example, it has long been known to protect it by mixing it with crosslinked proteins in the presence of an aidehyde.

Various processes for the crosslinking of proteins in the presence or absence of vitamin A have been described. Crosslinking of proteins in the presence of vitamin A or E poses an additional problem with respect to crosslinking in the absence of vitamin A or E. Vitamin A in the acetate form and vitamin E are oily products which only mix with proteins and their crosslinking agent in the form of an oil-in-water emulsion, which is never easy to handle. Crosslinking of the protein also requires heating for a relatively long period, which is not favorable to the stability of these vitamins.

A first process for the crosslinking of gelatin in the presence of acetaldehyde, to protect vitamin A, is, for example, proposed in Patent EP 261,616. In this patent, an "intimate" mixture of the protein, a water-miscible alcohol, acetaldehyde and approximately 3% of water and vitamin A is prepared. In this mixture, vitamin A can be present in the form of droplets of less than 10 microns. A relatively dry powder of particles having a diameter between 100 and 800 microns can also be used, the particles each containing protein, Vitamin A and alcohol. The solid particles can be subjected to acetaldehyde vapors for a period of approximately 3 hours at a temperature between 50° C. and 90° C.

The method of preparation utlizing solid particles in EP 261,616 cannot be achieved in a continuous process because it is carried out in two steps, each of which can require a different type of apparatus: a lyophilizer and an apparatus for atomization. Lyophilization is the more costly of these two steps because of extremely limited production efficiency, which results in an expensive product.

A process for the preparation of beadlets of vitamin A is described in Patent EP 285,682. According to this process, an emulsion containing the vitamin, water, gelatin and a sugar is prepared, which is transformed into droplets by atomization, and these droplets are individually brought into contact with a cellulose powder which must display very specific characteristics; this contacting of each of the droplets with the cellulose powder is achieved by various techniques until the droplets harden.

The hardened droplets are then separated from the cellulose powder by sieving, wherein, for example, the sieve retains the hardened droplets and allows the powder to pass through, which can involve a strict choice of the cellulose powder particle size and also difficulty regarding agglomeration characteristics of the powder during the implementation of the process.

The hardened droplets are next dried and then subjected to a heating operation to ensure crosslinking of the gelatin by reaction of the amino groups of the gelatin with the carboxyl functions of the sugar. This process is particularly difficult to implement because it requires a strict choice of the materials used and particularly close surveillance of the conditions under which the process is implemented.

The present invention has made it possible to solve the problems left by the prior art as a whole, and has above all made it possible to achieve a process which is very easy to implement.

A process of the present invention comprises the steps of:
  forming a primary oil-in-water emulsion comprising:
    particles comprising one or more active principles in oily form suspended in water, the water optionally containing at least one protein; and achieving controlled division of the primary emulsion by combining the primary emulsion with a water-immiscible solvent to create a second emulsion containing spherules of said primary emulsion.

A second emulsion in accordance with the present invention comprises:
  spherules comprising a primary oil-in-water emulsion containing particles comprising one or more active principles in oily form suspended in water, the water optionally containing at least one protein, the spherules being suspended in a water-immiscible solvent.

Figure 1:
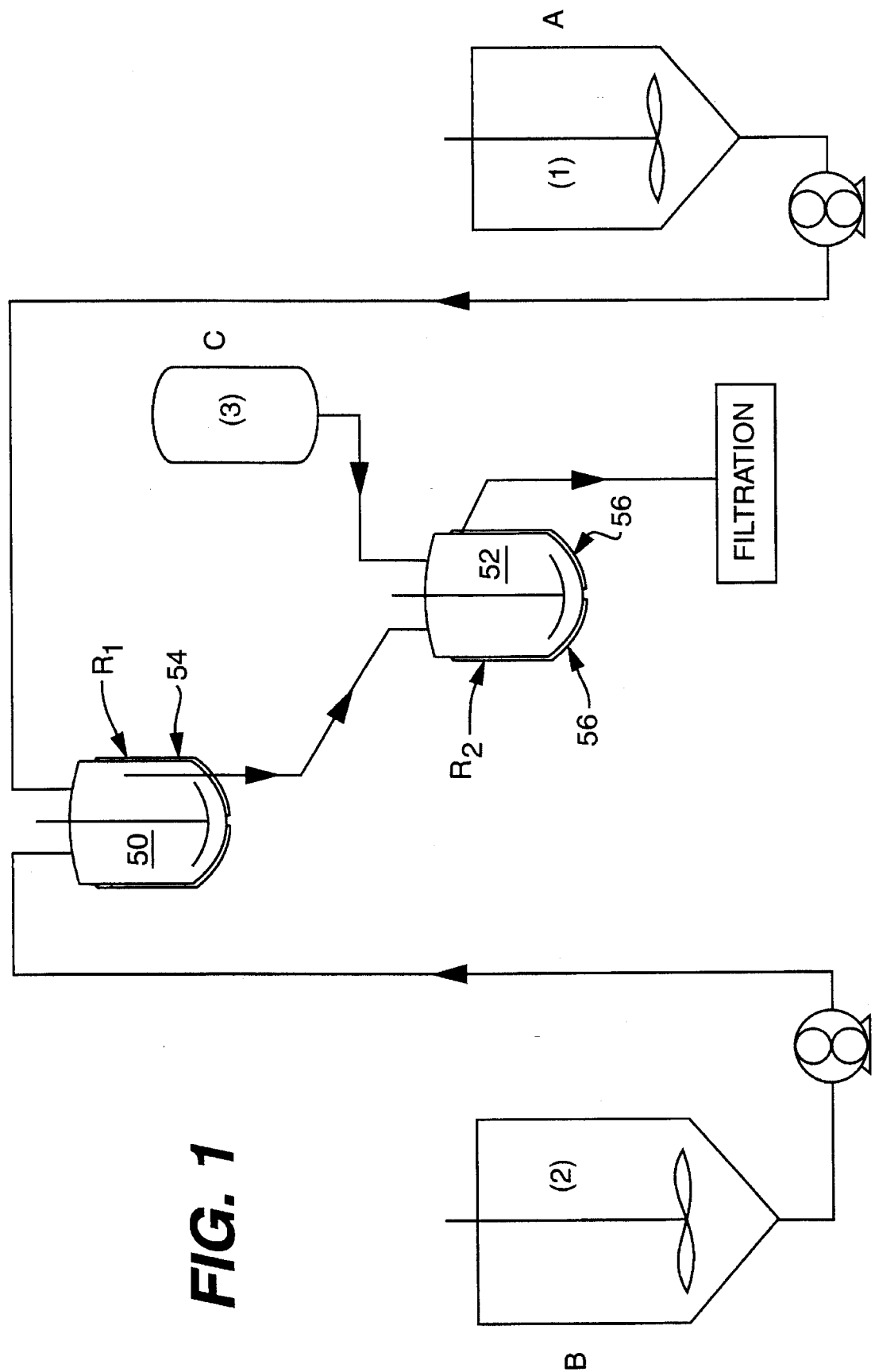
FIG. 1 is a flow chart illustrating formation of spherules by continuous granulation in a stirred mixer.

As defined herein, an active principle is an alimentary or medicinal active principle preferably chosen from (1) vitamins in the oily form such as, for example, vitamin A or vitamin E or (2) active principles which are converted to an oily form by, for example, being dissolved or dispersed in an edible oil. The edible oils are chosen, for example, from vegetable or animal oils such as groundnut, sunflower, rapeseed or cod liver oil.

The term "oily" herein is used in its ordinary meaning, i.e. of, relating to or consisting of oil. The active principle, whether obtained in an oily form, or whether converted to an oily form by, for example, being dissolved or dispersed in an edible oil, is to be sufficiently oily to be able to form the primary oil-in-water emulsion discussed herein when combined with water, the water optionally containing at least one protein.

To the oily active principle may optionally be added one or more antioxidant agents such as 3-tert-butyl-4-hydroxyanisole (BHA), 3,5-di-tert-butyl-4-hydroxytoluene (BHT), 6-ethoxy-1,2-dihydroxy-2,2,4-trimethylquinoline (ethoxyquine), 2-tert-butyl-1,4-dihydroxybenzene (sold under the trade name EMBANOX), as well as vitamin E. This active principle in oily form, which may be in the form of a solution or a mixture, may also contain one or more surface-active agents preferably selected from dilauryl thiodipropionate, sold under the trade name IRGANOX, an alkali metal or alkaline-earth metal stearate, sodium or calcium 2-stearoyllactate and carboxymethyl cellulose.

According to a preferred way of implementing the invention for the formation of spherules, and particularly of spherules of vitamin A, the active principle in oily form, the antioxidant, and the surfactant are combined in the following proportions:

| | |
|---|---|
| vitamin A acetate | 70 to 80% |
| antioxidant agent | 10 to 30% |
| surfactant | 0 to 5% |

Preferably, a protein is utilized for ultimate cross-linking and, more preferably, the protein is dissolved in water. It is preferable to use gelatin. The aqueous solution of protein may also optionally contain a surface-active agent such as those mentioned above.

The aqueous protein solution preferably contains approximately 10 to 60% (preferably 20 to 30%) by weight of protein, e.g. gelatin, and optionally contains approximately 10 to 60% (preferably 10–20%) by weight of a sugar (e.g. glucose, lactose, fructose, sucrose or maltodextrin) or of glycerol.

The primary oil-in-water emulsion is preferably formed by dispersion of the at least one oily active principle, optionally combined, as set forth above, with antioxidant and/or surfactant, in an aqueous solution containing the protein and, optionally, surface-active agent, sugar or glycerol, as explained above, at a temperature greater than the gel point of the solution. If a surfactant is used, it assists in the formation of the oil-in-water emulsion.

The primary oil-in-water emulsion is preferably prepared by mixing from approximately 10 to 30% by weight of oily active principle, optionally containing additives, such as those specified above, and from 70 to 90% by weight of aqueous protein solution, optionally containing additives, such as those specified above. Other mixtures, containing various quantities of each of the solutions, may, of course, be prepared and are within the scope of the invention. The recommended quantities are merely preferable.

Figure 4:
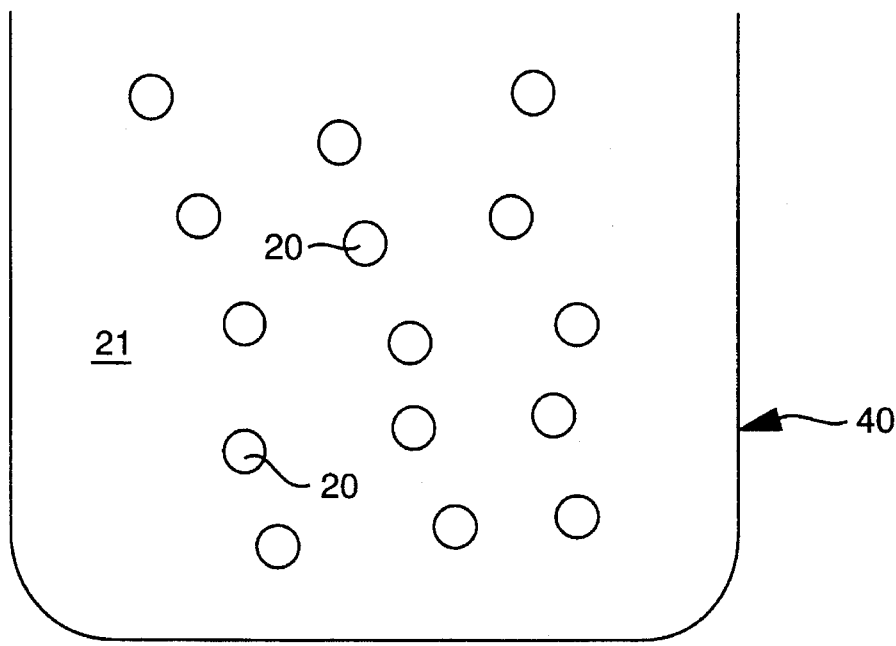
FIG. 4 represents a vessel containing a first oil-in-water emulsion of vitamin A in oily form in water.

FIG. 4 illustrates such a primary oil-in-water emulsion, wherein vessel 40 contains particles containing active principle 20, which may contain the additives set forth above, emulsified in the aqueous protein solution 21.

Figure 5:
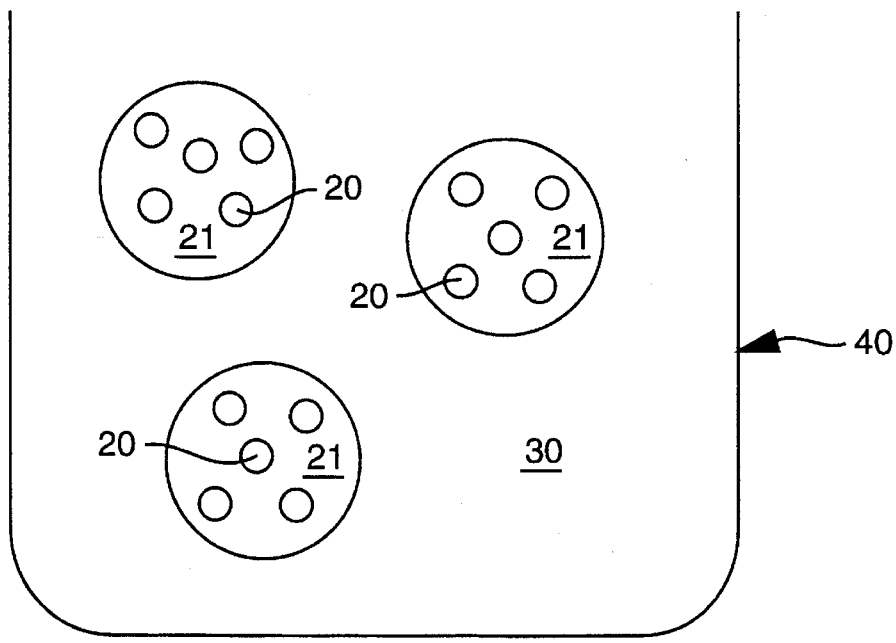
FIG. 5 represents a vessel containing a second emulsion formed from a water-immiscible solvent and the first oil-in-water emulsion shown in FIG. 4.

Controlled division of the primary oil-in-water emulsion, as defined herein, means to combine the primary oil-in-water emulsion with a water-immiscible solvent under conditions wherein the water-immiscible solvent does not break the primary emulsion but rather creates a second emulsion with the primary emulsion forming spherules therein. This is illustrated in FIG. 5 wherein, in vessel 42, the primary emulsion of particles containing active ingredient 20 suspended in aqueous protein solution 21 has undergone controlled division and now appears as a new emulsion of spherules 22 suspended in the water-immiscible solvent 30.

The water-immiscible solvent used to form the spherules is preferably chosen from aliphatic solvents containing 4 to 8 carbon atoms. It is particularly preferred to use an aliphatic fraction containing 6 carbon atoms. The water-immiscible solvent may also contain a surface-active agent such as a sucrose ester (0.1 to 1%).

After formation of the spherules 22 by controlled division of the primary oil-in-water emulsion, a protein cross-linking agent may be used to cross-link the protein. The agent is chosen, for example, from acetaldehyde, glutaraldehyde and glyoxal. The cross-linking agent optionally used may be employed in the pure state or, for example, in aqueous solution at a concentration of between 5 and 20%.

Various implementation processes of the invention will now be described.

According to a first implementation process represented by FIG. 1, a primary oil-in-water emulsion, as described above, is prepared in Vessel A. At least one active principle in oily form, optionally containing antioxidant and/or surfactant, as described above, is prepared separately in accordance with the teachings herein. In Vessel A, the aqueous protein solution, optionally containing surface-active agent, sugar, and/or glycerol is prepared in accordance with the teachings herein.

The primary oil-in-water emulsion is then formed in Vessel A by dispersion of the at least one active principle in oily form, optionally combined as set forth above, with antioxidant and/or surfactant, in the aqueous solution containing the protein and, optionally, surface-active agent, sugar or glycerol, as explained above, at a temperature greater than the gel point of the solution.

Formation of the spherules is achieved by introduction of the primary emulsion (1) coming from Vessel A and the water-immiscible solvent (2), optionally containing an emulsifier, coming from Vessel B into a mixer, which can be referred to as a granulation mixer, or reactor $R_1$ fitted with a turbine 50 which rotates at a sufficient speed to accomplish controlled division of the primary emulsion (1) to achieve the desired dispersion. This mixer $R_1$ is preferably maintained at a temperature of between 35° C. and 70° C., and even more preferably between 45° C. and 55° C.

The spherules obtained in mixer $R_1$ are then introduced into a cooling-crosslinking reactor $R_2$ maintained at approximately 20° C. by overflowing the contents of the granulation mixer $R_1$ or by any other means and are stirred by a turbine 52 to avoid coalescence of the spherules, and the crosslinking agent (3) is optionally introduced from vessel C into reactor $R_2$.

Formation of the spherules and their crosslinking may be achieved by a continuous process, for example with the aid of a series of reactors in a cascade, the filling of which is effected by overflowing the reactor upstream towards the reactor downstream, or by a non-continuous process. One skilled in the art will recognize that a continuous process presents notable economic advantages.

Figure 3:
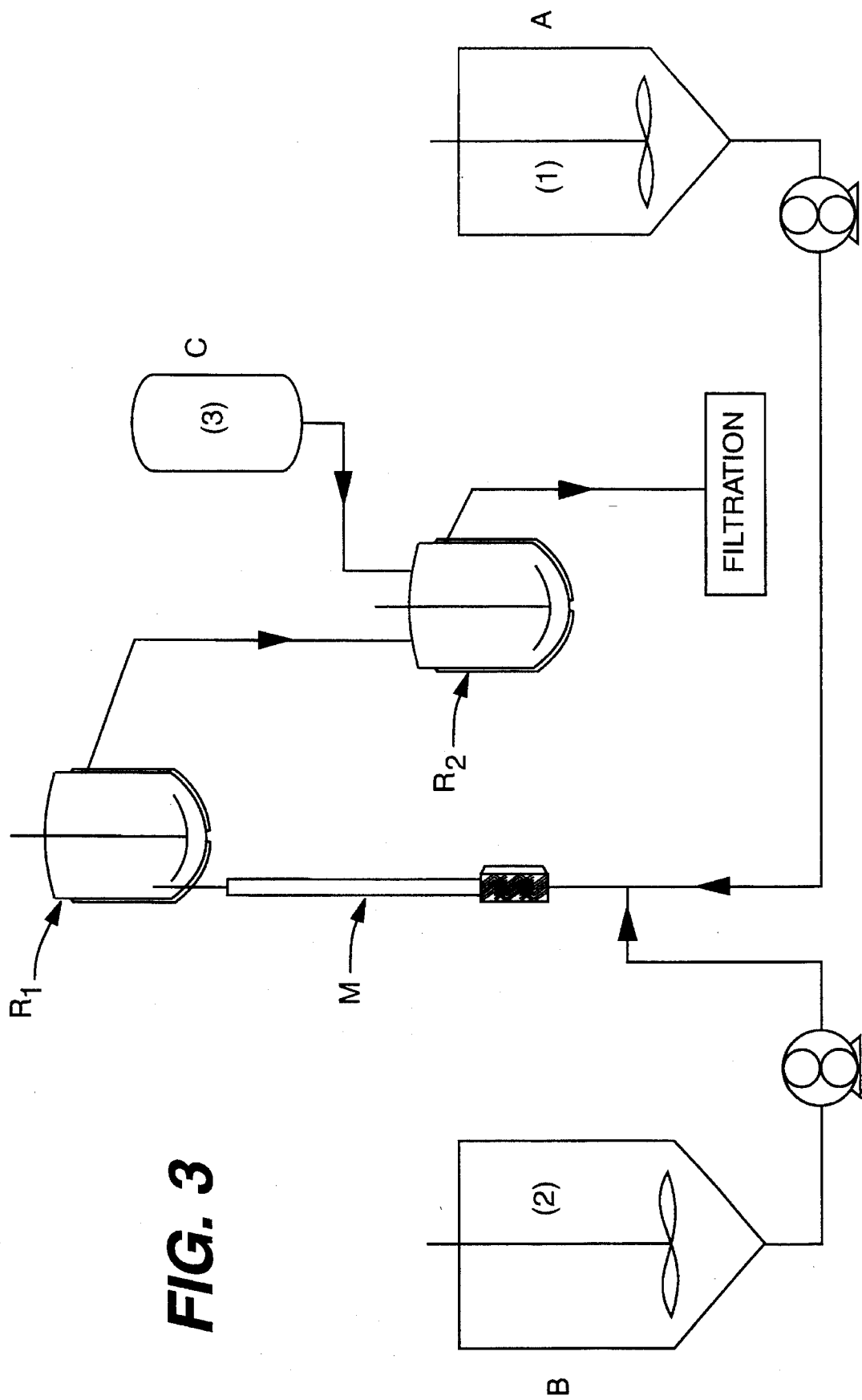
FIG. 3 is a flow chart illustrating formation of spherules using the static mixer of FIG. 2.

According to a second implementation process, formation of the spherules is achieved according to FIG. 3 by passing into static mixer M, from Vessel A, a primary oil-in-water emulsion (1), prepared, for example, as described herein, and from Vessel B, water-immiscible solvent (2), prepared, for example, as described herein. The speed of mixing and the temperature of the first emulsion and of the solvent in static mixer M are adapted to the size of spherules which one skilled in the art desires to obtain. The volume phase ratio of the primary emulsion to the solvent is preferably between 0.2 and 1.

Figure 2:
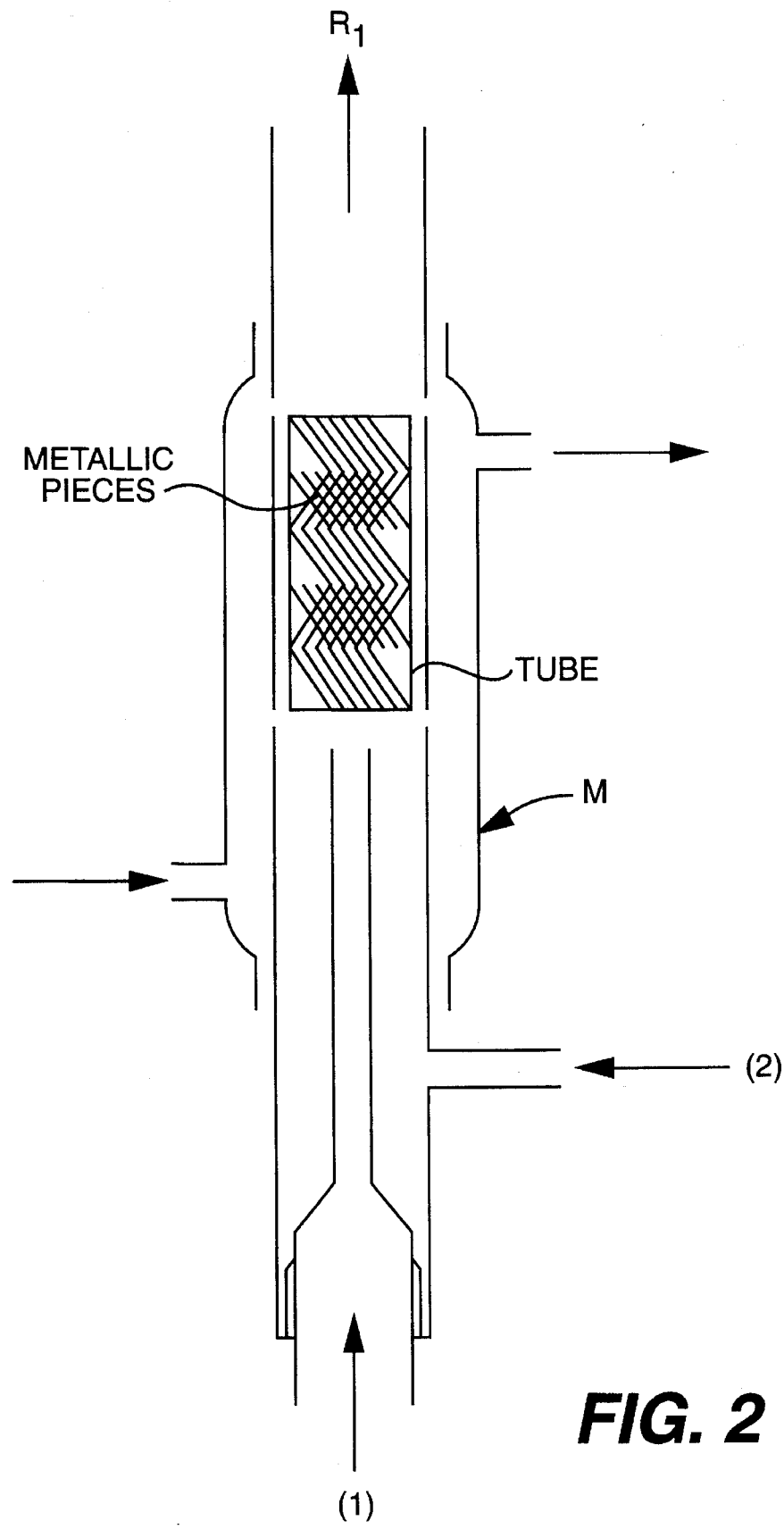
FIG. 2 is a diagram illustrating a static mixer useful in the formation of spherules.

The static mixer (M), as shown in FIG. 2, consists of a tube containing intersecting metallic pieces. Among the types of static mixers which may be used, there may be mentioned those sold under the trade name SULZER, such as are described in the French Patent application published under the number 2,468,401, the disclosure of which is specifically incorporated by reference herein.

This type of apparatus is used to achieve homogeneous mixtures of various fluids and intimate mixtures of viscous products in a product of lower viscosity. This type of apparatus, however, has never been used hitherto for forming spherules which have a diameter of 100 µm to 500 µm from (1) a viscous primary emulsion having a mean diameter of the order of 1 µm and (2) an immiscible solvent. It is totally surprising that a static mixer which has hitherto been used for obtaining intimate mixtures can make it possible to obtain spherules having a fixed mean diameter between 100 µm and 500 µm and which have a very fine dispersion of particles (preferably a mean diameter of about 1 µm) comprising the at least one active principle.

The spherules exiting the static mixer M (see FIG. 3) are cooled to approximately room temperature by stirring in a reactor $R_1$ to avoid their coalescence. The protein crosslinking agent (3) is then optionally added from Vessel C into a reactor $R_2$, and then the spherules are separated by filtration.

The processes described collectively make it possible to produce spherules of active principles in a continuous fashion and in apparatuses of small size. The processes do not require a drying step before carrying out the crosslinking and furthermore do not require the presence of any pulverulent material different from the desired composition. These processes therefore possess an enormous advantage with respect to all of the processes known hitherto.

The present invention will be more fully described with the aid of the following examples, which should not be considered in any way as limiting the invention.

EXAMPLE

AQUEOUS PROTEIN SOLUTION

Into a 50 liter reactor stirred with a dispersing turbine rotating at 450–500 revolutions/minute were introduced the following:

14.2 liters of water 1 kg of glycerin

The mixture was heated to 60° C. The following were added with stirring:

3.7 g of lactose 6.2 kg of gelatin

Stirring was continued for 35 minutes at 60° C.

THE ALIMENTARY CHARGE

In a reactor, the following vitamin-containing charge was mixed:

2.92 kg of vitamin A in acetate form 0.75 kg of BHT 0.23 kg of IRGANOX®

PREPARATION OF THE PRIMARY OIL-IN-WATER EMULSION

The whole mixture of the alimentary charge was heated to approximately 60° C. and poured into the above 50 liter reactor in which the turbine was brought to 3,000 revolutions/minute. Stirring was continued for 20 minutes, maintaining the temperature at 60° C. A primary oil-in-water emulsion was obtained in which the diameter of the particles was approximately one micron.

PREPARATION OF THE WATER-IMMISCIBLE SOLVENT 1.6 g of sucrose ester were dissolved in 1 liter of isohexane.

1st IMPLEMENTATION PROCESS OF THE INVENTION
  APPARATUS (FIG. 1)

The granulation reactor $R_1$ is a 0.5 liter glass reactor having a jacket 54 and equipped with a RAYNERI turbine 50 rotating at a speed of 800 to 1,000 revolutions/minute.

The cooling-crosslinking reactor $R_2$ is a 0.5 liter glass reactor fitted with a jacket 56 and equipped with a RAYNERI turbine 52 rotating at 500 revolutions/minute.

The primary oil-in-water emulsion (1), prepared as described above in this example, was stored in a 5 liter reactor (Vessel A) maintained at 60° C.

The water-immiscible solvent (2), prepared as described above in this example, was stored in a 10 liter reactor (Vessel B) maintained at 50° C.

250 ml of water-immiscible solvent (2) were introduced into the granulation reactor $R_1$, and then the primary oil-in-water emulsion (1) prepared previously was fed into $R_1$ from Vessel A at a flow rate of 1.7 liters per hour.

After the contents of $R_1$ were stirred for 5 minutes, the solvent (2) was fed in at a flow rate of 3.4 liters per hour. When the volume reached 350 ml in $R_1$, the contents of reactor $R_1$ overflowed into the cooling-crosslinking reactor $R_2$, which is a 0.5 liter glass reactor containing 400 ml of solvent.

The temperature in reactor $R_2$ was regulated to 20° C. by circulation of cold water in the jacket 56. As soon as the contents of the reactor $R_2$ overflowed via the overflow pipe, an aqueous solution of glutaraldehyde (16.7% by weight) was introduced in a continuous fashion into $R_2$ from Vessel C at a flow rate of 50 ml/hour.

The crosslinked particles thus obtained were isolated by filtration and then dried in a fluidized bed. The particles displayed the following size characteristics:

Mean diameter: 320 µm

Dispersion index: 0.344

Spherules larger than 500 µm=4.3%

Spherules smaller than 100 µm=4.9%

Dispersion index is understood to mean the result of the difference between the diameter at which 84% of the particles pass through and the diameter at which 16% of the particles pass through, divided by twice the mean diameter.

2nd IMPLEMENTATION PROCESS OF THE INVENTION
  APPARATUS (FIGS. 2 and 3)

The emulsion (1) prepared as described above was introduced (see FIG. 3) into Vessel A with stirring, and the solvent (2) prepared as described above was introduced into Vessel B.

The emulsion (1) was introduced into the static mixer M (shown in both FIGS. 2 and 3) from Vessel A at a flow rate of approximately 1.2 liters per hour, and the solvent (2) was introduced into the static Mixer M from Vessel B at a flow rate of 4 liters per hour. The mixture was heated to a temperature of approximately 50° C. by circulation of hot water in a jacket.

The mixer (M) takes the form of a column filled with metallic pieces, having a diameter of 4 mm and a height of approximately 4 cm.

At the outlet of the static mixer (M) (see FIG. 3) the emulsion was directed towards a cooling reactor $R_1$ where stirring was maintained to avoid coalescence of the spherules, until the temperature reached approximately 20° C.

The emulsion was then directed towards a reactor $R_2$ where an aqueous solution of the crosslinking agent at a concentration of 17% was added from Vessel C in a continuous fashion in a proportion of 0.68 g of glutaraldehyde per 100 g of emulsion.

The crosslinked particles were separated by filtration, as shown schematically in FIG. 3, and then dried in a fluidized bed.

The particles displayed the following size characteristics:

Mean diameter=315 μm

Dispersion index=0.30

Particles larger than 500 μm=1.1%

Particles smaller than 100 μm=1.2%

What is claimed is:

1. A process for preparing spherules of at least one active principle selected from alimentary principles and medicinal principles which comprises the steps of:

(a) forming a primary oil-in-water emulsion comprising: particles containing at least one of said active principles in oily form suspended in water, said water containing at least one protein;

(b) achieving controlled division of said primary oil-inwater emulsion by combining said primary oil-in-water emulsion with a water-immiscible solvent to create a second emulsion containing spherules of said primary oil-in-water emulsion;

(c) crosslinking said at least one protein contained in the epherules of said second emulsion by contacting said spherules with a crosslinking agent, wherein said crosslinking agent consists of glutaraldehyde; and drying said spherules after said step (c) of crosslinking.

2. A process according to claim 1, wherein said spherules of said second emulsion are separated from said water-immiscible solvents, and wherein said separation of said spherules occurs after step (c) and prior to step (d).

3. A process according to claim 2, wherein said separation is achieved by filtration.

4. A process according to claim 2, wherein said step of drying is conducted in a fluidized bed.

5. A process according to claim 1, wherein the spherules contained in said second emulsion have a diameter ranging from 100 μm to 500 μm.

6. A process according to claim 1, wherein said particles of one or more active principles in oily form in said primary oil-in-water emulsion have a mean diameter of about 1 μm.

7. A process according to claim 1, wherein said one or more active principles is selected from vitamins A, E, $D_3$, $B_{12}$, H, $K_3$, PP, $B_1$, $B_2$, $B_3$, $B_5$ and $B_6$.

8. A process according to claim 1, wherein said at least one protein is gelatin.

9. A process according to claim 1, wherein said one or more active principles in oily form are selected from vitamin A and vitamin E.

10. A process according to claim 1, wherein said one or more active principles is formed in oily form by combination of said one or more active principles with an oil selected from rapeseed oil, groundnut oil, sunflower oil and cod liver oil.

11. A process according to claim 1, wherein the primary oil-in-water emulsion additionally contains an antioxidant agent selected from 3-tert-butyl-4-hydroxyanisole, 3,5-di-tert-butyl-4-hydroxytoluene, 6-ethoxy-1,2-dihydroxy-2,2,4-trimethylquinoline and 2-tert-butyl-1,4-dihydroxytoluene.

12. A process according to claim 1, wherein the primary oil-in-water emulsion additionally contains a surface-active agent selected from dilauryl thiodipropionate, an alkali metal stearate, an alkaline-earth metal stearate, sodium 2-stearoyllactate, calcium 2-stearoyllactate and carboxymethyl cellulose.

13. A process according to claim 1, wherein the water-immiscible solvent is an aliphatic solvent containing 4 to 8 carbon atoms.

14. A process according to claim 1, wherein the primary oil-in-water emulsion is formed by mixing said one or more active principles in oily form with an aqueous solution containing said at least one protein.

15. A process according to claim 14, wherein said primary oil-in-water emulsion is formed by mixing from approximately 10 to 30% by weight of said one or more active principles in oily form with from 70 to 90% by weight of aqueous solution containing said at least one protein.

16. A process according to claim 14, wherein said one or more active principles in oily form is combined with one or more antioxidizing agents.

17. A process according to claim 16, wherein said one or more active principles in oily form is combined with one or more surface active agents.

18. A process according to claim 1, wherein the crosslinking agent is employed in a pure state or in an aqueous solution containing 5 to 20% by weight of the crosslinking agent.

19. A process according to claim 1, wherein said controlled division is achieved by combining said primary oil-in-water emulsion and said water-immiscible solvent in a mixer under conditions sufficient to form a second emulsion containing spherules having a diameter ranging from 100 μm to 500 μm.

20. A process according to claim 19, wherein the mixer is a static mixer.

21. A process according to claim 19, wherein the mixer is a stirred mixer.

22. The process of claim 1, wherein said spherules contained in said second emulsion created in step (b) and said crosslinking in step (c) are achieved continuously by means of a series of reactors in a cascade, and wherein each reactor downstream is filled by overflowing the reactor immediately upstream.

* * * * *

UNITED STATES PATENT AND TRADEMARK OFFICE
CERTIFICATE OF CORRECTION

PATENT NO. : 5,500,415
DATED : March 19, 1996
INVENTOR(S) : Jean-Marie DOLLAT et al It is certified that error appears in the above-indentified patent and that said Letters Patent is hereby corrected as shown below:

Claim 1, Column 7, Line 28, "inwater" should read --in-water--.

Claim 1, Column 7, Line 33, "epherules" should read --spherules--.

Claim 1, Column 7, Line 36, before "drying", insert --(d)--.

Claim 12, Column 8, Line 15, "carboxym" should read --carboxy--.

Claim 12, Column 8, Line 16, "ethyl" should read --methyl--.

Claim 2, Column 7, Line 39, "solvents" should read --solvent--.

Signed and Sealed this

Twenty-first Day of January, 1997

Attest:

BRUCE LEHMAN

*Attesting Officer*  *Commissioner of Patents and Trademarks*